United States Patent [19]

Lombardino

[11] 3,971,802

[45] July 27, 1976

[54] CERTAIN N'-ALKYL-N'-(2'-ALKOXYCARBONYLBENZENESULFONYL)--N-(2-THIAZOLYL)GLYCINEAMIDES

[75] Inventor: Joseph G. Lombardino, Niantic, Conn.

[73] Assignee: Pfizer Inc., New York, N.Y.

[22] Filed: Apr. 4, 1975

[21] Appl. No.: 565,230

Related U.S. Application Data

[62] Division of Ser. No. 462,212, April 19, 1974, Pat. No. 3,927,002, which is a division of Ser. No. 353,607, April 23, 1973, Pat. No. 3,853,862.

[52] U.S. Cl. .......................................... 260/306.8 R
[51] Int. Cl.² ........................................ C07D 277/46
[58] Field of Search ............................. 260/306.8 R

[56] References Cited

UNITED STATES PATENTS 3,927,002    12/1975    Lombardino ................. 260/294.8 F Primary Examiner—Richard J. Gallagher
Attorney, Agent, or Firm—Connolly and Hutz

[57] ABSTRACT

A process for the synthesis of N-aryl-3,4-dihydro-2-alkyl-4-oxo-2H-1,2-benzothiazine-3-carboxamide 1,1-dioxides by treatment of N-aryl-N'-alkyl-N'-(2'-alkoxycarbonylbenzenesulfonyl)glycineamides, useful intermediates for said process, with an alkali or alkaline earth metal hydride in a reaction-inert solvent at 50°–150° C., said products being antiinflammatory agents.

3 Claims, No Drawings

CERTAIN N'-ALKYL-N'-(2'-ALKOXYCARBONYLBENZENESULFONYL)-N-(2-THIAZOLYL)GLYCINEAMIDES

CROSS-REFERENCE TO RELATED APPLICATIONS

This application is a division of application Ser. No. 462,212 filed Apr. 19, 1974 and now U.S. Pat. No. 3,927,002 which, in turn, is a division of application Ser. No. 353,607 filed Apr. 23, 1973 and now U.s. Pat. No. 3,853,862.

BACKGROUND OF THE INVENTION

This invention relates to a process for the synthesis of 1,2-benzothiazine-3-carboxamides, and in particular to the preparation of N-aryl-3,4-dihydro-2-alkyl-4-oxo-2H-1,2-benzothiazine-3-carboxamide 1,1-dioxides, a class of compounds useful as antiinflammatory agents, and to N-aryl-N'-alkyl-N'-(2'-alkoxycarbonylbenzenesulfonyl)glycineamides as useful intermediates for said process.

Synthesis of 3,4-dihydro-2-alkyl-4-oxo-2H-1,2-benzothiazine-3-carboxamide 1,1-dioxides has been previously achieved by amination of the corresponding 3-carboxylic acid ester or by treatment of the parent 3,4-dihydro-2-alkyl-4-oxo-2H-1,2-benzothiazine 1,1-dioxide with the appropriate isocyanate, Lombardino, et al., J. Med. Chem., 14, 1171 (1971) and Zinnes, et al., ibid., 16, 43 (1973) and U.S. Patent 3,591,584. In addition, Zinnes, et al., loc. cit., has taught the preparation of 3-carboxamides by treatment of the pyrrolidine enamine of 3,4-dihydro-2-methyl-4-oxo-2H-1,2-benzothiazine 1,1-dioxide with phosgene followed by treatment of the resulting 3-carbonyl chloride with an appropriate amine.

U.S. Pat. No. 3,714,155 discloses 4-hydroxy-2,N-dimethyl-2H-1,2-benzothiazine-3-carboxanilide 1,1-dioxides as antiinflammatory agents, synthesized by methylation of the corresponding N-phenyl carboxamide with dimethylsulfate in the presence of sodium hydride.

SUMMARY OF THE INVENTION

It has now been discovered that preparation of compounds of the formula

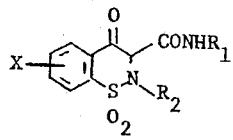

wherein $R_1$ is selected from the group consisting of phenyl; monosubstituted phenyl wherein said substituent is fluoro, chloro, methyl or methoxy; 2-thiazolyl; 4,5-dimethyl-2-thiazolyl; 2-pyridyl; 6-methyl-2-pyridyl; and 5-methyl-3-isoxazolyl; $R_2$ is alkyl containing one to three carbon atoms; and X is a substituent selected from the group consisting of hydrogen, methyl, methoxy, fluoro, chloro and bromo, which comprises contacting a compound of the formula

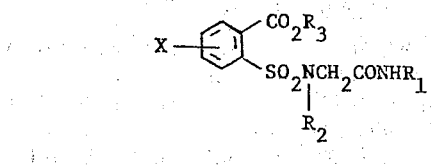

wherein $R_3$ is alkyl containing from 1 to 3 carbon atoms, with an alkali or alkaline earth metal hydride in a reaction-inert solvent at 50°–150° C. leads to the desired compounds which are potent nonsteroidal antiinflammatory agents.

Also claimed, as useful intermediates leading to the final products, are compounds of the formula

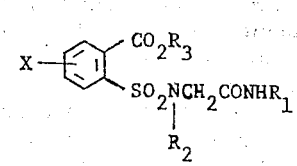

wherein $R_1$ is selected from the group consisting of phenyl; monosubstituted phenyl wherein said substituent is fluoro, chloro, methyl or methoxy; 2-thiazolyl; 4,5-dimethyl-2-thiazolyl; 2-pyridyl; 6-methyl-2-pyridyl; and 5-methyl-3-isoxazolyl; $R_2$ is alkyl containing one to three carbon atoms; and X is a substituent selected from the group consisting of hydrogen, methyl, methoxy, fluoro, chloro and bromo.

Also considered within the scope of the instant invention is the process wherein $R_3$ is alkyl of up to 8 carbon atoms, aryl or aralkyl, and wherein the metal hydride is replaced by a suitable organometallic reagent.

A preferred feature of the process leading to the compounds of the present invention is the use of sodium hydride as the metal hydride and tetrahydrofuran as the reaction-inert solvent, while the preferred intermediates are N-(aryl)-N'-methyl-N'-(2'-alkoxycarbonylbenzenesulfonyl)glycineamides.

DETAILED DESCRIPTION OF THE INVENTION

The aforementioned reaction is depicted in the following scheme

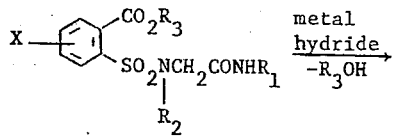 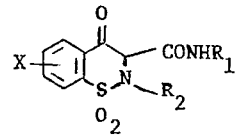

wherein $R_1$, $R_2$, $R_3$ and X are as previously described.

In the above reaction of the benzenesulfonylglycineamide with a metal hydride the ratio of reactants is two equivalents of hydride per mole of glycineamide. In practice, a slight excess of 5–10% over two equivalents of the metal hydride has no deleterious effect on the formation of the desired product.

It is also desirable to conduct said reaction in a reaction-inert solvent. By such a solvent, or mixtures thereof, is contemplated those, which under the conditions of the instant process, do not enter into appreciable reaction with either the starting reagents or products. It is preferred that non-aqueous, aprotic, polar solvents be employed. Suitable solvents or mixtures thereof which are included in this group are alicyclic ethers, di(lower)alkoxyalkanes, di(lower)alkylsulfoxides, di(lower)alkyl(lower)alkanoic amides and hexa(lower)alkylphosphoramides. Favored solvents for the present process invention are tetrahydrofuran, dioxane, dimethylformamide and dimethylsulfoxide. The especially preferred solvent is tetrahydrofuran.

It is also preferred, although not a requirement, that the employed solvent be water-miscible.

Reaction time is not critical and is inherently dependent on concentration, reaction temperature and reactivity of the starting materials. In general, when temperatures of 50°–100° C. are employed, the reaction time will vary between 4–10 hours.

Regarding temperature range, it is preferred, for practical reasons, that the instantly claimed process be heated in order to obtain optimum yields of the desired products. A temperature range of 50°–150° C. is operative, with a preferred range of 50°–100° C.

At the conclusion of the cyclization reaction the mixture is cooled and added to water, to which is then added sufficient acid to render the mixture acidic to litmus paper. The product is then extracted with a water-immiscible solvent, such as methylene chloride or chloroform, and the organic extracts concentrated to dryness. Further purification of the products is effected by recrystallization from an appropriate solvent.

The intermediate benzenesulfonylglycineamides, which are cyclized under the conditions of the present process, are prepared as shown by the following flow diagram:

zine 1,1-dioxide wherein $R_2$ is methyl; X is hydrogen and $R_1$ is phenyl, 2-pyridyl, 2-thiazolyl or 6-methyl-2-pyridyl.

The particularly preferred benzenesulfonylglycineamide intermediate are those wherein $R_1$ is phenyl, pyridyl, 2-thiazolyl or 6-methyl-2-pyridyl and $R_2$ and $R_3$ are each methyl.

The examples which follow are given by way of illustration, and are not to be construed as limitations of this invention, many variations of which are possible within the scope and spirit thereof.

EXAMPLE 1

N-(2-Thiazolyl)-3,4-dihydro-2-methyl-4-oxo-2H-1,2-benzothiazine-3-carboxamide 1,1-dioxide To 25 mg. (0.068 m mole) of N-(2-thiazolyl)-N'-methyl-N'-(2'-methoxycarbonylbenzenesulfonyl)-glycineamide in 2 ml. of dry tetrahydrofuran maintained under a nitrogen atmosphere is added 6.5 mg. (0.135 m mole) of a 50% sodium hydride suspension in oil, and the resulting reaction mixture heated under reflux overnight. The reaction mixture comprised of a yellow suspension is quenched with ice and subsequently acidified with 3N hydrochloric acid. The product is extracted with chloroform and the extracts combined and dried over sodium sulfate. The drying agent is filtered and the filtrate concentrated to a gum, which on trituration with 0.5 ml. of chloroform and 3 ml. of hexane yields 3.3 mg. of the desired product, m.p. 172°–193° C. Recrystallization, m.p. 256° C. dec., provides material identical to that prepared in U.S. Pat. No. 3,591,584.

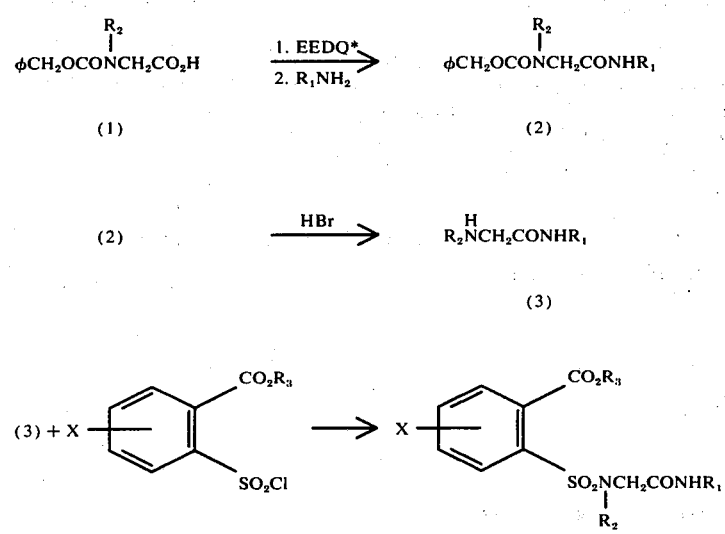

*N-Ethoxycarbonyl-2-ethoxy-1,2-dihydroquinoline

The glycine derivatives (1) are readily prepared by the methods reviewed by Greenstein and Winitz, "Chemistry of the Amino Acids," John Wiley & Sons, Inc., New York, New York 1961, Volumes 1–3.

As previously mentioned, the compounds of the present process invention are useful as antiinflammatory agents, and U.S. Pat. No. 3,591,584 teaches how to use these compounds for this utility. Of particular interest in the present invention are the synthesis of benzothia-

EXAMPLE 2

3,4-Dihydro-2-methyl-4-oxo-2H-1,2-benzothiazinecarboxanilide 1,1-dioxide

To a solution of 3.77 g. (0.01 mole) of N-phenyl-N'-methyl-N'-(2-ethoxycarbonylbenzenesulfonyl)-glycineamide in 40 ml. of dimethylformamide maintained under a nitrogen atmosphere is added portionwise 960 mg. (0.02 mole) of a 50% sodium hydride suspension in oil, and the reaction mixture heated at steam bath temperatures for 6 hrs. The mixture is cooled, poured into ice and water and acidified with 6N hydrochloric acid. The product is extracted with chloroform and the combined chloroform extracts (3) are back-washed with water and dried over sodium sulfate. The solvent is removed under reduced pressure and the residue gum induced to crystallize by trituration with cold isopropanol. The filtered product proves to be identical with that reported in U.S. Pat. No. 3,591,584.

EXAMPLE 3

N-(6-Methyl-2-pyridyl)-3,4-dihydro-2-methyl-4-oxo-2H-1,2-benzothiazine-3-carboxamide 1,1-dioxide In a manner similar to Examples 1 and 2, 2.03 g. (5 m moles) of N-(6-methyl-2-pyridyl)-N'-methyl-N'-(2'-propoxycarbonylbenzenesulfonyl)glycine-amide in 25 ml. of dioxane is treated with 205 mg. (5 m moles) of calcium hydride and the resulting mixture heated under reflux overnight. The cooled reaction mixture is quenched in ice, acidified, and the product extracted with methylene chloride. The organic extracts are combined, dried over sodium sulfate and concentrated in vacuo to a gum. Trituration with cold acetonitrile followed by filtration provides the desired product.

EXAMPLE 4

3'-Chloro-3,4-dihydro-2-methyl-4-oxo-2H-1,2-benzothiazine-3-carboxanilide 1,1-dioxide The procedure of Example 1 is repeated, starting with 4.11 g. (0.01 mole) of N-(3-chlorophenyl)-N'-methyl-N'-(2-methoxycarbonylbenzenesulfonyl)-glycineamide and 800 mg. (0.02 mole) of a 50% suspension of potassium hydride in 40 ml. of dimethylsulfoxide, to yield the desired crude product. Further purification is achieved by recrystallization from acetic acid.

EXAMPLE 5

The procedure of Example 1 is again repeated, starting with the appropriate N-aryl-N'-alkyl-N'-(2-methoxycarbonylbenzenesulfonyl)glycineamides to provide the following congeners:

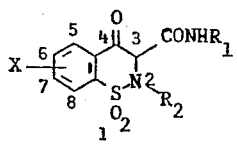

| X | R₁ | R₂ |
|---|-----|-----|
| 6-F | C₆H₅— | CH₃ |
| 6-F | 3-CH₃C₆H₄— | CH₃ |
| 6-F | 4-CH₃OC₆H₄— | C₂H₅ |
| 8-F | 4-CH₃OC₆H₄— | CH₃ |
| 8-F | 4-ClC₆H₄— | C₂H₅ |
| 8-F | 6-CH₃—2-C₅H₃N— | n-C₃H₇ |
| 6-Cl | 3-CH₃C₆H₄— | CH₃ |
| 6-Cl | 2-C₃H₂NS— | n-C₃H₇ |
| 6-Cl | 3-FC₆H₄— | i-C₃H₇ |
| 6-Cl | 2-CH₃OC₆H₄— | i-C₃H₇ |
| 7-Cl | 2-C₃H₂NS— | CH₃ |
| 7-Cl | 2-C₃H₂NS— | C₂H₅ |
| 7-Cl | 2-C₅H₄N— | C₂H₅ |
| 7-Cl | 2-C₅H₄N— | i-C₃H₇ |
| 7-Cl | 2-C₄H₃O— | CH₃ |
| 8-Cl | C₆H₅— | CH₃ |
| 5-CH₃ | C₆H₅— | CH₃ |
| 5-CH₃ | 4,5-(CH₃)₂C₃NS— | CH₃ |
| 5-CH₃ | 4,5-(CH₃)₂C₃NS— | n-C₃H₇ |
| 5-CH₃ | 4-ClC₆H₄— | C₂H₅ |
| 7-Cl | 5-CH₃—3-C₃HNO | CH₃ |
| 5-CH₃ | 4-CH₃OC₆H₄— | CH₃ |
| 6-CH₃ | 2-C₃H₂NS— | CH₃ |
| 6-CH₃ | 2-C₅H₄N— | C₂H₅ |
| 6-CH₃ | 2-C₄H₃O— | CH₃ |
| 6-CH₃ | 4-CH₃OC₆H₄— | CH₃ |
| 6-CH₃ | 2-C₅H₄N— | i-C₃H₇ |
| 7-CH₃ | 6-CH₃—2-C₅H₃N— | CH₃ |
| 7-CH₃ | 6-CH₃—2-C₅H₃N— | n-C₃H₇ |
| 7-CH₃ | 3-CH₃C₆H₄— | CH₃ |
| 7-CH₃ | 4,5-(CH₃)₂C₃NS— | CH₃ |
| 7-CH₃ | C₆H₅— | C₂H₅ |
| 6-CH₃O | C₆H₅— | CH₃ |
| 6-CH₃O | C₆H₅— | C₂H₅ |
| 6-CH₃O | C₆H₅— | n-C₃H₇ |
| 6-CH₃O | 2-ClC₆H₄— | CH₃ |
| 6-CH₃O | 2-C₄H₃O— | CH₃ |
| 7-CH₃O | 3-CH₃C₆H₄— | CH₃ |
| 7-CH₃O | 2-C₃H₂NS— | n-C₃H₇ |
| 7-CH₃O | 2-C₅H₄N— | C₂H₅ |
| 7-CH₃O | 6-CH₃—2-C₅H₃N— | CH₃ |
| 7-CH₃O | 3-ClC₆H₄— | CH₃ |
| 8-CH₃O | C₆H₅— | CH₃ |
| 8-CH₃O | C₆H₅— | C₂H₅ |
| 8-CH₃O | 4-CH₃OC₆H₄— | CH₃ |
| 8-CH₃O | 4-ClC₆H₄ | CH₃ |
| 6-CH₃ | 5-CH₃—3-C₃HNO | CH₃ |
| 6-CH₃O | 5-CH₃—3-C₃HNO | CH₃ |

EXAMPLE 6

Starting with the requisite N-aryl-N'-alkyl-N'-(2-methoxycarbonylbenzenesulfonyl)glycineamide and the indicated metal hydride, the procedure of Example 2 is repeated wherein the following compounds are synthesized (product, metal hydride):

3'-methyl-3,4-dihydro-2-methyl-4-oxo-2H-1,2-benzothiazine-3-carboxanilide 1,1-dioxide, LiH; 4'-methoxy-3,4-dihydro-2-ethyl-4-oxo-2H-1,2-benzothiazine-3-carboxanilide 1,1-dioxide, CaH₂; 4'-chloro-3,4-dihydro-2-ethyl-4-oxo-2H-1,2-benzothiazine-3-carboxanilide 1,1-dioxide, KH; N-(6-methyl-2-pyridyl)-3,4-dihydro-2-n-propyl-4-oxo-2H-1,2-benzothiazine-3-carboxamide 1,1-dioxide, NaH; 2'-fluoro-3,4-dihydro-2-methyl-4-oxo-2H-1,2-benzothiazine-3-carboxanilide 1,1-dioxide, RbH; 4'-fluoro-3,4-dihydro-2-ethyl-4-oxo-2H-1,2-benzothiazine-3-carboxanilide 1,1-dioxide, CaH₂; N-(2-thiazolyl)-3,4-dihydro- 2-i-propyl-4-oxo-2H-1,2-benzothiazine-3-carboxamide 1,1-dioxide, CsH; N-(4,5-dimethyl-2-thiazolyl)-3,4-dihydro-2-methyl-4-oxo-2H-1,2-benzothiazine-3-carboxamide 1,1-dioxide,BaH₂; N-(2-furyl)-3,4-dihydro-2-methyl-4-oxo-2H-1,2-benzothiazine-3-carboxamide 1,1-dioxide, CaH₂; N-(2-furyl)-3,4-dihydro-2-methyl-4-oxo-2H-1,2-benzothiazine-3-carboxamide 1,1-dioxide, LiH; 3'-methoxy-3,4-dihydro-2-n-propyl-4-oxo-2H-1,2-benzothiazine-3-carboxanilide 1,1-dioxide, KH: 2'-chloro-3,4-dihydro-2-ethyl-4-oxo-2H-1,2-benzothiazine-3-carboxanilide 1,1-dioxide, MgH₂; N-(2-pyridyl)-3,4-dihydro-2-methyl-4-oxo-2H-1,2-benzothiazine-3-carboxamido 1,1-dioxide, RbH; N-(6-methyl-2-pyridyl)-3,4-dihydro-2-ethyl-4-oxo-2H-1,2-benzothiazine-3-carboxamide 1,1-dioxide, LiH; 4'-methyl-3,4-dihydro-2-methyl-4-oxo-2H-1,2-benzothiazine-3-carboxanilide 1,1-dioxide, KH; N-(2-thiazolyl)-3,4-dihydro-2-i-propyl-4-oxo-2H-1,2-benzothiazine-3-carboxamide 1,1-dioxide, BaH₂; N-(5-methyl-3-isoxazolyl)-3,4-dihydro-2-methyl-4-oxo-2H-1,2-benzothiazine-3-carboxamide 1,1-dioxide, CaH₂; and N-(5-methyl-3-isoxazolyl)-3,4-dihydro-2-methyl-4-oxo-2H-1,2-benzothiazine-3-carboxamide 1,1-dioxide, LiH.

PREPARATION A

Benzyloxycarbonylglycineamides

1. N-Methyl-N'-benzyloxycarbonyl-N-(2-thiazolyl)-glycineamide (2: $R_1 = 2\text{-}C_3H_2NS$; $R_2 = CH_3$; $R_3 = CH_3$; $X = H$)

To a yellow solution of 9.44 g. (42.3 m moles) of commercially available N-benzyloxycarbonyl-N-methylglycine and 4.8 g. (48 m moles) of 2-aminothiazole in 75 ml. of dry tetrahydrofuran under a nitrogen atmosphere is added dropwise 13 g. (53 m moles) of N-ethoxycarbonyl-2-ethoxy-1,2-dihydroquinoline in 75 ml. of the same solvent. The resulting reaction mixture is allowed to stir at room temperature for 1 hr. and is then heated under reflux for 2 hrs. The solution is cooled in ice and the resulting solids filtered and dried, 4.6 g., m.p. 203°–205° C.

Anal. Calc'd for $C_{14}H_{15}O_3N_3S$: C, 55.06; H, 4.59; N, 13.76. Found: C, 55.02; H, 4.94; N, 13.71. 2. In a similar manner to Preparation A-1, starting with the requisite glycine derivative and aryl amine, the following benzyloxycarbonylglycineamides are synthesized as intermediates:

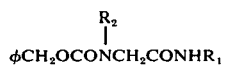

$\phi CH_2OCONCH_2CONHR_1$

| $R_1$ | $R_2$ |
|---|---|
| $C_6H_5-$ | $CH_3$, $C_2H_5$ and n-$C_3H_7$ |
| 6-$CH_3$—2-$C_5H_4N-$ | $CH_3$, $C_2H_5$ and n-$C_3H_7$ |
| 3-$ClC_6H_4-$ | $CH_3$ |
| 3-$CH_3C_6H_4-$ | $CH_3$ |
| 4-$CH_3OC_6H_4-$ | $CH_3$ and $C_2H_5$ |
| 2-$C_4H_3O-$ | $CH_3$ |
| 4,5-$(CH_3)_2C_3NS-$ | $CH_3$ and n-$C_3H_7$ |
| 2-$ClC_6H_4-$ | $CH_3$ and $C_2H_5$ |
| 4-$ClC_6H_4-$ | $CH_3$ and $C_2H_5$ |
| 2-$FC_6H_4-$ | $CH_3$ |
| 2-$C_5H_4N-$ | $CH_3$, $C_2H_5$ and i-$C_3H_7$ |
| 4-$CH_3C_6H_4-$ | $CH_3$ |
| 2-$C_3H_2NS-$ | $C_2H_5$, n-$C_3H_7$ and i-$C_3H_7$ |
| 4-$FC_6H_4-$ | $C_2H_5$ |
| 3-$CH_3OC_6H_4-$ | n-$C_3H_7$ |
| 3-$FC_6H_4-$ | i-$C_3H_7$ |
| 2-$CH_3OC_6H_4-$ | i-$C_3H_7$ |
| 5-$CH_3$—3-$C_3HNO-$ | $CH_3$ |

PREPARATION B

Glycineamides

1. N'-Methyl-N-(2-thiazolyl)glycineamide (3: $R_1 = CH_3$; $R_2 = 2\text{-}C_3H_2NS$)

To 5 g. of N'-methyl-N'-benzyloxycarbonyl-N-(2-thiazolyl)glycineamide under a nitrogen atmosphere is added slowly with stirring 50 ml. of a 33% hydrogen bromide solution in acetic acid. After the vigorous evolution of carbon dioxide has subsided, the reaction mixture is allowed to stir at room temperature overnight. Diethyl ether (275 ml.) is added and the precipitated solids filtered and dried, 5.4 g., m.p. 242°–244° C., dec.

The analytical sample is recrystallized from ethanol-diethyl ether.

Anal. Calc'd for $C_6H_9ON_3S \cdot 2HBr$: C, 21.64; H, 3.33; N, 12.62. Found: C, 22.36; H, 3.34; N, 12.87.

The free base is generated by treatment of an aqueous solution of the hydrobromide salt with an aqueous sodium hydroxide solution, followed by extraction of the free base into a water-immiscible solvent such as benzene.

2. N'-Alkyl-N-Arylglycineamides

Starting with the requisite intermediate from Preparation A-2 and following the procedure of Preparation B-1, the following intermediate products are prepared:

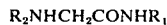

$R_2NHCH_2CONHR_1$

| $R_1$ | $R_2$ |
|---|---|
| $C_6H_5-$ | $CH_3$, $C_2H_5$ and n-$C_3H_7$ |
| 6-$CH_3$—2-$C_5H_4N-$ | $CH_3$, $C_2H_5$ and n-$C_3H_7$ |
| 3-$ClC_6H_4-$ | $CH_3$ |
| 3-$CH_3C_6H_4-$ | $CH_3$ |
| 4-$CH_3OC_6H_4-$ | $CH_3$ and $C_2H_5$ |
| 2-$C_4H_3O-$ | $CH_3$ |
| 4,5($CH_3)_2C_3NS-$ | $CH_3$ and n-$C_3H_7$ |
| 2-$ClC_6H_4-$ | $CH_3$ and $C_2H_5$ |
| 4-$ClC_6H_4-$ | $CH_3$ and $C_2H_5$ |
| 2-$FC_6H_4-$ | $CH_3$ and $C_2H_5$ |
| 2-$C_5H_4N-$ | $CH_3$, $C_2H_5$ and i-$C_3H_7$ |
| 4-$CH_3C_6H_4-$ | $CH_3$ |
| 2-$C_3H_2NS-$ | $C_2H_5$, n-$C_3H_7$ and i-$C_3H_7$ |
| 4-$FC_6H_4-$ | $C_2H_5$ |
| 3-$CH_3OC_6H_4-$ | n-$C_3H_7$ |
| 3-$FC_6H_4-$ | i-$C_3H_7$ |
| 2-$CH_3OC_6H_4-$ | i-$C_3H_7$ |
| 5-$CH_3$—3-$C_3HNO-$ | $CH_3$ |

PREPARATION C

2-Carboalkoxybenzenesulfonyl Chlorides

1. A heavy precipitate resulting from the addition of 85 ml. of 12N hydrochloric acid to 37.8 g. of methyl anthranilate in 50 ml. of cold water is stirred and maintained at 0°–5° C. in an ice bath while 19.0 g. of sodium nitrite in 30 ml. of cold water is added dropwise. The resulting pale yellow solution is stirred for 30 min. at 0°–5° C. and is filtered through a sentered glass filter.

The above filtrate containing the diazonium salt is slowly added dropwise to a solution resulting the addition of a cold solution of 40 g. of sulfur dioxide in 200 ml. of glacial acetic acid to a cold suspension of 8 g. of cupric chloride in 111 ml. of glacial acetic acid. During the second half of the addition and for 20 min. after the addition is complete, gas evolution is evident. After stirring the reaction mixture for 1 hr. in the cold, 1.4 l. of ice water is added and the precipitate intermediate product is filtered and dried in vacuo, 9.2 g., m.p. 60°–62° C.

Meerwein, et al., Chem. Ber., 90, 841 (1957) reports a m.p. of 64°–65° C. for this compound which is prepared by a similar procedure.

2. Substituted 2-Carboalkoxybenzenesulfonyl chlorides

Starting with the appropriately substituted anthranilic acid esters which are either known in the chemical literature or readily prepared by methods known to those skilled in the art and employing the procedure of Meerwein, et al. or that of Preparation C-1, the following sulfonyl chlorides are synthesized:

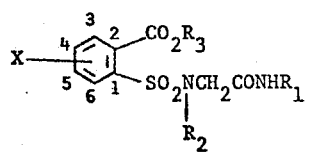

| X | R₃ |
|---|---|
| 4-F | CH₃ |
| 6-F | CH₃ |
| 4-Cl | CH₃ |
| 5-Cl | CH₃ |
| 6-Cl | CH₃ |
| 3-CH₃ | CH₃ |
| 4-CH₃ | CH₃ |
| 5-CH₃ | CH₃ |
| 4-CH₃O | CH₃ |
| 5-CH₃O | CH₃ |
| 6-CH₃O | CH₃ |
| H | C₂H₅ |
| H | n-C₃H₇ |

PREPARATION D

N-Benzenesulfonylglycineamides

1.

N-(2-Thiazolyl)-N'-methyl-N'-(2'-methoxycarbonyl-benzenesulfonyl)glycineamide N'-Methyl-N-(2-thiazolyl)glycineamide, generated from 4.84 g. of the corresponding dihydrobromide salt, in 50 ml. of benzene is treated with 3.41 g. of 2-methoxycarbonylbenzenesulfonyl chloride, and the resulting mixture heated under reflux for 30 hrs. The reaction mixture is cooled and the precipitated solids filtered, washed with benzene and partitioned between water and chloroform. The water layer is extracted several additional times with chloroform, and the chloroform extracts combined and dried over sodium sulfate. The organic solvent is removed in vacuo and the tan residual solid is triturated with hexane and filtered, 640 mg., m.p. 215° C. dec. The analytical sample is recrystallized from methanol, m.p. 216°–218° C. dec.

Anal. Calc'd for $C_{14}H_{15}O_5N_3S_2$: C, 45.52; H, 4.09; N, 11.37. Found: C, 45.02; H, 4.12; N, 11.71.

2.

N-Aryl-N'-alkyl-(2'-alkoxycarbonylbenzenesulfonyl)-glycineamides

Starting with the requisite intermediates from Preparations B and C and employing the procedure of Preparation D-1, the following intermediates are prepared:

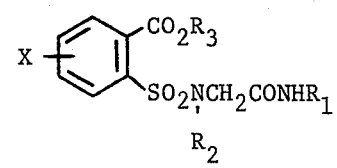

| X | R₁ | R₂ | R₃ |
|---|---|---|---|
| H | C₆H₅— | CH₃ | C₂H₅ |
| H | 6-CH₃—2-C₅H₃N— | CH₃ | n-C₃H₇ |
| H | 3-ClC₆H₄— | CH₃ | CH₃ |
| 4-F | C₆H₅— | CH₃ | CH₃ |
| 4-F | 3-CH₃C₆H₄— | CH₃ | CH₃ |
| 4-F | 4-CH₃OC₆H₄— | C₂H₅ | CH₃ |
| 6-F | 4-CH₃OC₆H₄— | CH₃ | CH₃ |
| 6-F | 4-ClC₆H₄— | C₂H₅ | CH₃ |
| 6-F | 6-CH₃—2-C₅H₃N— | n-C₃H₇ | CH₃ |
| 4-Cl | 3-CH₃C₆H₄— | CH₃ | CH₃ |
| 4-Cl | 2-C₃H₂NS— | n-C₃H₇ | CH₃ |
| 4-Cl | 3-FC₆H₄— | i-C₃H₇ | CH₃ |
| 4-Cl | 2-CH₃OC₆H₄— | i-C₃H₇ | CH₃ |
| 5-Cl | 2-C₃H₂NS— | CH₃ | CH₃ |

-continued

| X | R₁ | R₂ | R₃ |
|---|---|---|---|
| 5-Cl | 2-C₃H₂NS— | C₂H₅ | CH₃ |
| 5-Cl | 2-C₅H₄N— | C₂H₅ | CH₃ |
| 5-Cl | 2-C₅H₄N— | i-C₃H₇ | CH₃ |
| 5-Cl | 2-C₄H₃O— | CH₃ | CH₃ |
| 6-Cl | C₆H₅— | CH₃ | CH₃ |
| 3-CH₃ | C₆H₅— | CH₃ | CH₃ |
| 3-CH₃ | 4,5-(CH₃)₂—2-C₃NS— | CH₃ | CH₃ |
| 3-CH₃ | 4,5-(CH₃)₂—2-C₃NS— | n-C₃H₇ | CH₃ |
| 3-CH₃ | 4-ClC₆H₄— | C₂H₅ | CH₃ |
| 3-CH₃ | 4-CH₃OC₆H₄— | CH₃ | CH₃ |
| 4-CH₃ | 2-C₃H₂NS— | CH₃ | CH₃ |
| 4-CH₃ | 2-C₅H₄N— | C₂H₅ | CH₃ |
| 4-CH₃ | 2-C₄H₃O— | CH₃ | CH₃ |
| 4-CH₃ | 4-CH₃OC₆H₄— | CH₃ | CH₃ |
| 4-CH₃ | 2-C₅H₄N— | i-C₃H₇ | CH₃ |
| 5-CH₃ | 6-CH₃—2-C₅H₃N— | CH₃ | CH₃ |
| 5-CH₃ | 6-CH₃—2-C₅H₃N— | n-C₃H₇ | CH₃ |
| 5-CH₃ | 3-CH₃C₆H₄— | CH₃ | CH₃ |
| 5-CH₃ | 4,5-(CH₃)₂C₃NS— | CH₃ | CH₃ |
| 5-CH₃ | C₆H₅— | C₂H₅ | CH₃ |
| 4-CH₃O | C₆H₅— | CH₃ | CH₃ |
| 4-CH₃O | C₆H₅— | C₂H₅ | CH₃ |
| 4-CH₃O | C₆H₅— | n-C₃H₇ | CH₃ |
| 4-CH₃O | 2-ClC₆H₄— | CH₃ | CH₃ |
| 4-CH₃O | 2-C₄H₃O— | CH₃ | CH₃ |
| 5-CH₃O | 3-CH₃C₆H₄— | CH₃ | CH₃ |
| 5-CH₃O | 2-C₃H₂NS— | n-C₃H₇ | CH₃ |
| 5-CH₃O | 2-C₅H₄N— | C₂H₅ | CH₃ |
| 5-CH₃O | 6-CH₃—2-C₅H₃N— | CH₃ | CH₃ |
| 5-CH₃O | 3-ClC₆H₄— | CH₃ | CH₃ |
| 6-CH₃O | C₆H₅— | CH₃ | CH₃ |
| 6-CH₃O | C₆H₅— | C₂H₅ | CH₃ |
| 6-CH₃O | 4-CH₃OC₆H₄— | CH₃ | CH₃ |
| 6-CH₃O | 4-ClC₆H₄— | CH₃ | CH₃ |
| H | 3-CH₃C₆H₄— | CH₃ | CH₃ |
| H | 4-CH₃OC₆H₄— | C₂H₅ | CH₃ |
| 5-Cl | 5-CH₃—3-C₃HNO— | CH₃ | CH₃ |
| 4-CH₃O | 5-CH₃—3-C₃HNO— | CH₃ | CH₃ |
| H | 5-CH₃—3-C₃HNO— | CH₃ | CH₃ |
| H | 4-ClC₆H₄— | C₂H₅ | CH₃ |
| H | 6-CH₃—2-C₅H₃N— | n-C₃H₇ | CH₃ |
| H | 2-FC₆H₄— | CH₃ | CH₃ |
| H | 4-FC₆H₄— | C₂H₅ | CH₃ |
| H | 2-C₃H₂NS— | i-C₃H₇ | CH₃ |
| H | 4,5-(CH₃)₂—2-C₃NS— | CH₃ | CH₃ |
| H | 2-C₄H₃O | CH₃ | CH₃ |
| H | 3-CH₃OC₆H₄— | n-C₃H₇ | CH₃ |
| H | 2-ClC₆H₄— | C₂H₅ | CH₃ |
| H | 2-C₅H₄N— | CH₃ | CH₃ |
| H | 6-CH₃—2-C₅H₃N— | C₂H₅ | CH₃ |
| H | 4-CH₃C₆H₄— | CH₃ | CH₃ |

PREPARATION E

Metal Hydrides

The metal hydrides utilized in the present process are either commercially available or are prepared by literature procedures, Moeller, "Inorganic Chemistry," John Wiley & Sons, New York, New York 1959.

What is claimed is:

1. A compound of the formula:

wherein R₁ is selected from the group consisting of; 2-thiazolyl and 4,5-dimethyl-2-thiazolyl;

R₂ is alkyl having from 1 to 3 carbon atoms;

X is selected from the group consisting of hydrogen, methyl, methoxy, fluoro, chloro and bromo and R₃ is alkyl having from 1 to 3 carbon atoms.

2. A compound of claim 1 wherein X is hydrogen and R₂ and R₃ are each methyl.

3. The compound of claim 2 wherein R₁ is 2-thiazolyl.

* * * * *

UNITED STATES PATENT AND TRADEMARK OFFICE
CERTIFICATE OF CORRECTION

PATENT NO. : 3,971,802
DATED : July 27, 1976
INVENTOR(S) : Joseph G. Lombardino

It is certified that error appears in the above-identified patent and that said Letters Patent are hereby corrected as shown below:

Col. 10, line 28, should be read with the inserted entry under the designated columns:

| | | | | | |
|---|---|---|---|---|---|
| -- | 4-$CH_3$ | 5-$CH_3$-3-$C_3$HNO- | $CH_3$ | $CH_3$ | -- . |

Signed and Sealed this

Eighteenth Day of January 1977

[SEAL]

Attest:

RUTH C. MASON
*Attesting Officer*

C. MARSHALL DANN
*Commissioner of Patents and Trademarks*